United States Patent
Zhang et al.

(10) Patent No.: US 12,156,861 B2
(45) Date of Patent: Dec. 3, 2024

(54) PHARMACEUTICAL COMPOSITION FOR TREATING KIDNEY CANCER AND APPLICATION THEREOF

(71) Applicant: SICHUAN JIUZHANG BIOLOGICAL SCIENCE AND TECHNOLOGY CO., LTD., Sichuan (CN)

(72) Inventors: Jie Zhang, Sichuan (CN); Xiaoguang Chen, Sichuan (CN); Wang Huang, Sichuan (CN); Ya Zhang, Sichuan (CN)

(73) Assignee: SICHUAN JIUZHANG BIOLOGICAL SCIENCE AND TECHNOLOGY CO., LTD, Sichuan (CN)

( * ) Notice: Subject to any disclaimer, the term of this patent is extended or adjusted under 35 U.S.C. 154(b) by 1037 days.

(21) Appl. No.: 15/734,105

(22) PCT Filed: May 31, 2019

(86) PCT No.: PCT/CN2019/089637
§ 371 (c)(1),
(2) Date: Jun. 9, 2021

(87) PCT Pub. No.: WO2019/228524
PCT Pub. Date: Dec. 5, 2019

(65) Prior Publication Data
US 2021/0330626 A1 Oct. 28, 2021

(30) Foreign Application Priority Data

Jun. 1, 2018 (CN) .......................... 201810559399.5

(51) Int. Cl.
| | | |
|---|---|---|
| A61K 31/216 | (2006.01) | |
| A61K 31/403 | (2006.01) | |
| A61K 31/44 | (2006.01) | |
| A61K 31/506 | (2006.01) | |
| A61P 35/00 | (2006.01) | |
| A61K 31/192 | (2006.01) | |

(52) U.S. Cl.
CPC .......... *A61K 31/216* (2013.01); *A61K 31/403* (2013.01); *A61K 31/44* (2013.01); *A61K 31/506* (2013.01); *A61P 35/00* (2018.01)

(58) Field of Classification Search
CPC .... A61K 31/216; A61K 31/403; A61K 31/44; A61K 31/506; A61K 31/192; A61P 35/00
See application file for complete search history.

(56) References Cited

U.S. PATENT DOCUMENTS

| | | | |
|---|---|---|---|
| 10,189,769 B2 * | 1/2019 | Zhang | ..................... C07C 39/10 |
| 2021/0085630 A1 * | 3/2021 | Zhang | .................. A61K 31/655 |

FOREIGN PATENT DOCUMENTS

| | | | | |
|---|---|---|---|---|
| CN | 1646112 A | | 7/2005 | |
| CN | 102488682 A | | 6/2012 | |
| CN | 107375258 A | * | 11/2017 | ........... A61K 31/216 |
| CN | 108159038 A | | 6/2018 | |
| CN | 108498497 A | | 9/2018 | |
| CN | 108653263 A | | 10/2018 | |
| CN | 108685892 A | | 10/2018 | |

OTHER PUBLICATIONS

Pick AM, Nystrom KK. Pazopanib for the treatment of metastatic renal cell carcinoma. Clin Ther. Mar. 2012;34(3):511-20. doi: 10.1016/j.clinthera.2012.01.014. Epub Feb. 16, 2012. PMID: 22341567. (Year: 2012).*

* cited by examiner

*Primary Examiner* — Deepak R Rao
*Assistant Examiner* — Kevin S Martin
(74) *Attorney, Agent, or Firm* — NKL Law; Allen Xue

(57) ABSTRACT

A pharmaceutical composition contains chlorogenic acid and coumaroyl quinic acid. The combined use of chlorogenic acid and coumaroyl quinic acid at a certain ratio can generate a synergistic enhancing effect to effectively inhibit the growth of human kidney cancer cell strain A479, rat kidney cell strain RuCa, and rat transplanted tumor RuCa, providing a novel choice for clinical treatment of kidney cancer and having good market application prospects.

8 Claims, No Drawings

PHARMACEUTICAL COMPOSITION FOR TREATING KIDNEY CANCER AND APPLICATION THEREOF

TECHNICAL FIELD

The present invention belongs to the field of biomedicine, and specifically relates to a pharmaceutical composition and its use in preparing drugs for treatment of kidney cancer.

BACKGROUND ART

Renal cell carcinoma, abbreviated as renal cancer, is one of the most common tumors in the urinary system, with an incidence occupying 2% of adult malignant tumors. In China, the incidence of renal cell carcinoma ranks second in urinary system tumors, second only to bladder cancer. Epidemiological survey results showed that there were 63,000 new cases and 14,000 deaths from kidney cancer in the United States in 2016, making it the ninth most common cancer. With the continuous progress of diagnostic technology, patients with kidney cancer have received early treatment. The overall 5-year survival rate of kidney cancer has reached 74%, but only 12% of patients with late metastasis. Therefore, investigating and finding effective drugs for treatment of renal carcer has important clinical significance for improving the survival rate of patients with renal carcer.

For the treatment of kidney cancer, surgical treatment is the first choice for localized renal cancer. According to the stage and grade of the patient's tumor, radical nephrectomy or nephron-sparing surgery can be selected. For radiotherapy and chemotherapy, kidney cancer is generally resistant to chemotherapeutic drugs, and there is no ideal breakthrough in chemotherapy. Chemotherapy based on gemcitabine, 5-fluorouracil and other drugs has improved the efficacy at a certain extent, but there is no significant change in the period of progression survival and overall survival. In addition, kidney cancer is not sensitive to radiation, so radiation is traditionally considered to be ineffective. However, as a palliative treatment for advanced unresectable kidney cancer, radiation can reduce local pain, relieve hematuria and other symptoms, so as to improve the life quality of patients. For tumors that grow fast and have severe toxic symptoms, but can be surgically removed, preoperative radiotherapy can reduce the size of the tumor, reduce the spread of tumor cells during the operation, and reduce the local edema, which is helpful for intraoperative separation.

At present, the first-line treatment recommendations for kidney cancer include sorafenib, sunitinib, pazopanib, bevacizumab, interferon and the same, while the second-line treatment includes cabotinib, nivolumab, axitinib, everolimus, etc. A study published in the New England Journal of Medicine (N Engl J Med) in 2015 proved that cabozantinib is significantly better than everolimus in patients with advanced renal cell carcinoma. In the same year, N Engl J Med published another study, confirming that nivolumab is superior to everolimus. However, the above-mentioned therapeutic drugs generally have side effects such as diarrhea, skin rash, fatigue, hypertension, inflammation, and others. Moreover, with the prolonged administration time, there is strong drug resistance in the later stage of survival.

Chlorogenic acid is widely present in various medicinal plants, such as *Lonicera japonica*, and at present, its chemical structure has already been clearly studied. Medicinal studies on it have been carried out, and it has been reported that chlorogenic acid can be used to treat tumors and other diseases. Patent CN201110373137 discloses that chlorogenic acid has a certain therapeutic effect on kidney cancer. It directly targets the molecular mechanism that causes cancer and is more selective and effective than traditional chemotherapy, and has no antagonistic effect when used in combination with paclitaxel drugs. The structural formula of chlorogenic acid is as follows:

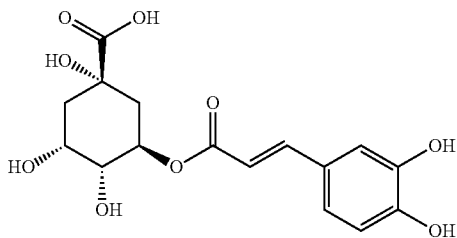 [SMILES: O=C(/C=C/c1ccc(O)c(O)c1)O[C@@H]1C[C@](O)(C(=O)O)C[C@@H](O)[C@H]1O]

Similar to chlorogenic acid, coumaroylquinic acid is widely found in higher plants. In the biosynthetic pathway, it is generally believed that coumaroyl CoA and caffeoyl CoA are respectively combined with quinic acid by catalysis, and finally form coumaroylquinic acid and chlorogenic acid. At present, there is no report on the activity of coumaroylquinic acid in the prior art,

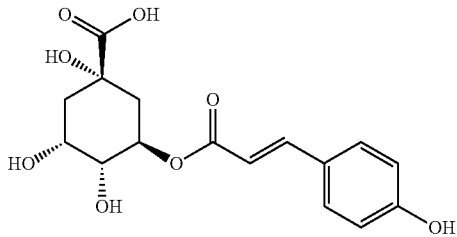 [SMILES: O=C(/C=C/c1ccc(O)cc1)O[C@@H]1C[C@](O)(C(=O)O)C[C@@H](O)[C@H]1O]

Content of the Invention

The first aspect of the present invention is to provide a pharmaceutical composition for the treatment of renal cancer, that includes chlorogenic acid and coumaroylquinic acid.

In certain embodiments, the mass ratio of chlorogenic acid to coumaroylquinic acid is 100:0.01-10;

Further, the mass ratio of chlorogenic acid to coumaroylquinic acid is 100:0.01-1.

In additional some embodiments, said pharmaceutical composition includes chlorogenic acid, coumaroylquinic acid and targeted drugs, the mass ratio of chlorogenic acid, coumaroylquinic acid and targeted drug is 100:0.01-1:0.1-1.

In specific embodiments, said targeted drug is selected from one of sorafenib, sunitinib and pazopanib. The second aspect of the present invention is to provide a pharmaceutical preparation, that is prepared by using the pharmaceutical composition mentioned above as an active ingredient, with addition of pharmaceutically acceptable excipients.

In some embodiments, said pharmaceutical preparation is an oral preparation or an injection.

In further embodiments, said excipients are selected from one or more of starch, β-cyclodextrin, dextrin, carbomer, microcrystalline cellulose, hydroxypropylmethyl cellulose, low-substituted hydroxypropyl cellulose, sodium carboxymethyl cellulose, polyethylene glycol (PEG), sodium carboxymethyl cellulose, methyl cellulose, ethyl cellulose, mannitol, sodium lauryl sulfate, croscarmellose sodium, lactose, glucose, vitamins, glutathione, folic acid, polyvinylpyrrolidone (PVP), cross-linked polyvinylpyrrolidone, magnesium stearate, talc, colloidal silicon dioxide, aspartame, orange flavor, sodium bisulfite, sodium bicarbonate, sodium carbonate, and enteric coating powder.

The third aspect of the present invention is to provide the use of the pharmaceutical composition in the preparation of a drug for treatment of kidney cancer.

In the above-mentioned medicinal uses, the administration time and the administration numbers of the pharmaceutical composition according to the present invention need to be determined according to the specific diagnostic result of the disease, which is within the technical scope of those skilled in the art. For example, if a therapeutic regime for mice or rats is applied to humans, the effective doses of all drugs to humans can be converted by the effective doses of the drugs to mice, which is easy for those of ordinary skill in the art to carry out.

In the present invention, it is found that although chlorogenic acid and coumaroylquinic acid have a similar structure, their inhibitory effects on renal cancer cell lines are quite different. Chlorogenic acid has obvious inhibitory effects on renal cancer cells, while coumaroylquinic acid has only a very weak inhibitory effect. Unexpectedly, when both of them are used in combination, a significant synergistic effect is observed in the treatment of kidney cancer. Furthermore, in the present invention, it is also found that when chlorogenic acid and coumaroylquinic acid are combined with a first-line targeted drug for the treatment of kidney cancer, the synergistic effect is the best. In order to facilitate the clinical application of the pharmaceutical composition, the present invention also provides related preparations of the pharmaceutical composition.

EXAMPLES

Obviously, based on above content of the present invention, according to the common technical knowledge and the conventional means in the field, without department from above basic technical spirits, other various modifications, alternations or changes can further be made.

By following specific examples of said embodiments, above content of the present invention is further illustrated. But it should not be construed that the scope of above subject of the present invention is limited to following examples. The techniques realized based on above content of the present invention are all within the scope of the present invention.

In the present invention, the synergy denotes the biological effect of the combination of components, and compared with the content required to produce a given biological effect when a single component is used alone, the activity of the composition is significantly better than the additive effect of the components. In a common language, the composition produces a biological effect of 1+1>2.

In some embodiments, the mass ratio of chlorogenic acid to coumaroylquinic acid is 100:0.01-10; further, the mass ratio of chlorogenic acid to coumaroylquinic acid is 100:0.01-1. Specifically, the mass ratio of chlorogenic acid to coumaroylquinic acid may be 100:0.01, 100:0.1, 100:0.2, 100:0.5, 100:1, 100:2, 100:5, 100:10.

The raw materials and equipment used in the specific examples of the present invention are all known products, that are obtained by purchasing commercially available products.

Example 1 the Formula for Oral Preparation of the Pharmaceutical Composition According to the Present Invention 1. Formula 1

Chlorogenic acid 1000 g, coumaroylquinic acid 10 g.

Preparative method: chlorogenic acid and coumaroylquinic acid were aseptically weighed according to the formula, mixed thorougly, and aseptically subpacked as powders.

2. Formula 2

Chlorogenic acid 1000 g, coumaroylquinic acid 5 g, bulking agent 500 g, binding agent 5 g.

Preparative method: chlorogenic acid, coumaroylquinic acid, bulking agent, and binding agent were weighed according to the formula, granulated, sieved, and subpacked as granules.

3. Formula 3

Chlorogenic acid 1000 g, coumaroylquinic acid 1 g, bulking agent 500 g, binding agent 5 g, and lubricant 3 g.

Preparative method: chlorogenic acid, coumaroylquinic acid, bulking agent, and binding agent were weighed according to the formula, granulated, sieved, and then lubricant was added, followed by pressing, to obtain tablets.

Above bulking agents were one or more of mannitol, lactose, starch, microcrystalline cellulose, and dextrin; the binding agents were sodium carboxymethylcellulose and PVP; the lubricants were magnesium stearate, talcum powder, and colloidal silicon dioxide.

Example 2 the Formula for Injection of the Pharmaceutical Composition According to the Present Invention 1. Formula 1

Chlorogenic acid 1000 g, coumaroylquinic acid 1 g.

Preparative method (1): chlorogenic acid and coumaroylquinic acid were aseptically weighed according to the formula, mixed thorougly, and aseptically subpacked as powder injection.

Preparative method (2): chlorogenic acid and coumaroylquinic acid were weighed according to the formula, dissolved in water for injection, filtered, sterilized, and freeze-dried to obtain freeze-dried powder injection.

2. Formula 2

Chlorogenic acid 1000 g. coumaroylquinic acid 1 g, stent agent 2667 g, and antioxidant 67 g.

Preparative method: chlorogenic acid, coumaroylquinic acid, stent agent, and antioxidant were weighed according to the formula, dissolved in water for injection, filtered, sterilized, and freeze-dried to obtain freeze-dried powder injection.

Said stent agents were mannitol, lactose and glucose; the antioxidants were sodium bisulfite, vitamin, glutathione, and folic acid.

In the following, the beneficial effect of the present invention was proved by experimental examples:

Experimental Example 1 Experiment on the Treatment of Renal Cancer In Vitro by the Pharmaceutical Composition and Single Compound in it 1. Materials
1.1 Test Drugs Test drug 1: chlorogenic acid
Test drug 2: coumaroylquinic acid
Test drug 3: the combination of chlorogenic acid and coumaroylquinic acid (100:0.01)

Test drug 4: the combination of chlorogenic acid and coumaroylquinic acid (100:0.1)
Test drug 5: the combination of chlorogenic acid and coumaroylquinic acid (100:1)
Test drug 6: the combination of chlorogenic acid and coumaroylquinic acid (100:5)
Test drug 7: the combination of chlorogenic acid and coumaroylquinic acid (100:10)

1.2 Cell Lines

Human kidney cancer cell line A498 and mouse kidney cancer cell line RuCa; the cells were passaged prior to use, and the cells that were in a good growth state and in log phase growth were selected for use.

1.3 Main Reagents

Medium and reagents: medium RPML1640 (Gibco), calf serum (Lanzhou Minhai), penicillin (North China Pharmaceutical Co., Ltd.), streptomycin sulfate (North China Pharmaceutical Co., Ltd.), WST-1 (Roche Company, USA)).

1.4 Main Apparatus

Carbon dioxide cell incubator (SANYO, Japan), IX70 inverted phase contrast fluorescence microscope (Olympus, Japan), biological safety cabinet (NUAIRE, USA), μ-Quant microplate analyzer (BioTek company), culture dish: 96-well culture plate, culture bottle (BD Company).

2. Experimental Method 2.1 Preparation of Culture Solution

RPML1640 cell culture medium was dissolved in ultrapure water (1000 ml), and stirred to dissolve, to which were added 2.2 g $NaHCO_3$ and 10 ml HEPES, followed by stirring to dissolve. Then, suitable amount of penicillin (final concentration being 100 U/ml) and suitable amount of streptomycin (final concentration being 100 μg/ml) were added, and after thoroughly mixing, the solution was subjected to sterile filtration with 0.22 μm filter membrane. The filtrate was subpacked, and frozen at −20° C., that was the basal medium. The medium was thawed in a water bath at 37° C. prior to use, to which was added 10% calf serum, and the pH of the culture solution was adjusted to 7.2-7.4, which was a complete medium.

2.2 Detection Reagent for Cell Proliferation

Cell proliferation reagent (WST-1) (Roche 11644807001) should be refrigerated as required.

3. Cell Recovery and Seeding 3.1 Cell Recovery

The frozen cell lines were taken out from the ultra-low temperature freezer at −152° C., thawed in a 40° C. water bath, centrifuged, and washed with basal medium. Then, the cells were suspended in complete medium, and transferred to a cell culture flask, that was placed in a 5% $CO_2$ cell incubator and incubated at 37° C. The medium was changed every 2-3 days. After the cells were grown to spread the cell flask, they were digested with 0.25% trypsin and subcultured to the number of cells required for the experiment.

3.2 Cell Inoculation

The cells in logarithmic growth phase were collected, digested with 0.25% trypsin, washed with basic medium, and centrifuged (1000 rpm, 5 min, twice). Then, the cells were suspended in complete medium, and the cell concentration was adjusted to $6 \times 10^4$/ml. The cells were seeded in 96 well plates at 50 μl/well ($6 \times 10^3$ cells/well), and three multiple wells were set up for each drug concentration.

Moreover, the negative control group (renal cell carcinoma cells+complete medium) and blank control group (complete medium) were included, with three wells for each group.

3.3 Addition of Drugs

On the next day after inoculation, once cells were adherent to the wall, the drugs were added according to the following groups and then incubated for 48 h.

(1) Test Drug Groups

The storage solution of each drug was prepared into 60 μg/ml with complete medium for use; the complete medium of each test drug mentioned above (50 μl) was placed in the 96-well plate inoculated cells, and the final concentration of each group was 30 μg/ml, three wells for each concentration.

(2) Normal Control Group

The normal control group of tumor cells were set up and treated with the same amount of complete medium (100 μl) without drug, that was synchronized with the drug group.

(3) Blank Control Group

Each well was not inoculated with cells, and only the same amount (100 μl) of complete medium was added, and three wells were set as blank control.

3.4 Determination

After addition of drugs, the cells were cultured for 48 h, and the morphology of the cells was observed under the inverted microscope. Then, 10 μl WST-1 solution was added into the wells of above drug groups, negative control group, and blank control group. After the cells were incubated in 37° C. incubator for 4 h, the absorption values of different drug groups, negative control group and blank control group were measured at 440 nm by μ-Quant microplate analyzer.

3.5 Data Processing:

The calculation was performed by the formula: GI (Growth inhibition rate)=(1−ODdrug group/ODcontrol group)×100%

4 Experimental Results 4.1 In Vitro Antitumor Effect of Each Experimental Group on Human Renal Carcinoma Cell A498

4.1.1 Observation of Cell Morphology

After each experimental group was treated for 48 h, cell morphology was observed under inverted microscope. Compared with the negative control group, chlorogenic acid alone had certain effect on cell growth, and some cells became round, abscissed, and suspended; coumaroylquinic acid almost had no effect on cell growth, and the cells adhered to the wall and grew irregularly. However, the combination of chlorogenic acid and coumaroylquinic acid had significant inhibitory effect on the growth of human renal cancer cell lines A498, and when the ratio of both compounds was ranged from 100:0.01 to 100:1, lots of cells became round, shed, and suspended, while from 100:5 to 100:10, part of cells became round, shed, and suspended. The results showed that the growth of human renal cancer cell lines OS-RC-2 could be inhibited when the ratio of two compounds was in the range of 100:0.01 to 100:10. With the increase of the proportion of coumaroylquinic acid in the composition, the inhibitory effect of the composition on human renal cancer cell lines OS-RC-2 first increased and then decreased, and the ratio of 100:0.01 to 100:1 was the best.

4.1.2 the Inhibition Rate of Each Experimental Group on Human Renal Cancer Cell Lines A498

The inhibition rate of each experimental group on human renal cancer cell lines A498 are shown in Table 1 and FIG. 1.

TABLE 1

The inhibition rate of each experimental
group on human renal cancer cell lines A498

| Groups | OD value (average) | Inhibition rate (%) |
|---|---|---|
| Chlorogenic acid | 1.494 | 36.51% |
| Coumaroylquinic acid | 2.280 | 3.13% |
| Composition of chlorogenic acid and coumaroylquinic acid (100:0.01) | 1.058 | 55.03% |
| Composition of chlorogenic acid and coumaroylquinic acid (100:0.1) | 0.900 | 61.78% |
| Composition of chlorogenic acid and coumaroylquinic acid (100:1) | 1.270 | 46.03% |
| Composition of chlorogenic acid and coumaroylquinic acid (100:5) | 1.587 | 32.57% |
| Composition of chlorogenic acid and coumaroylquinic acid (100:10) | 1.857 | 21.09% |
| Negative control group | 2.354 | — |

After human renal cancer cell lines A498 were treated with each experimental group, compared with the negative control group, chlorogenic acid single compound had a certain effect on the growth of human renal cancer cell lines A498; coumaroylquinic acid almost had no effect on cell growth; however, the composition of chlorogenic acid and coumaroylquinic acid had significant inhibitory effect on the growth of human renal cancer cell lines A498. When the ratio of two compounds was in the range of 100:0.01 to 100:10, all the compositions could inhibit the growth of human renal cancer cell lines A498. As the ratio of coumaroylquinic acid increased in the composition, the inhibitory effect of the composition on human renal cancer cell lines A498 increased at first and then decreased.

In the ratio of 100:0.01 to 100:1, two compounds had synergistic effect, and the composition at the ratio of 100:0.1 showed the best effect.

4.4 Inhibitory Effect of Chlorogenic Acid on Mouse Renal Cancer Cell Lines RuCa In Vitro 4.4.1 Observation of Cell Morphology After each experimental group was treated for 48 h, cell morphology was observed under inverted microscope. Compared with the negative control group, chlorogenic acid single compound had certain effect on cell growth, and some cells became round, detached, and suspended; coumaroylquinic acid almost had no effect on cell growth, and the cells adhered to the wall and grew irregularly. However, the composition of chlorogenic acid and coumaroylquinic acid had significant inhibitory effect on the growth of mouse renal cancer cell lines RuCa, and when the ratio of both compounds was ranged from 100:0.01 to 100:1, lots of cells became round, detached, and suspended, while from 100:5 to 100:10, part of cells became round, shed, and suspended. The results showed that the growth of mouse renal cancer cell lines RuCa could be inhibited when the ratio of two compounds was in the range of 100:0.01 to 100:10. As the proportion of coumaroylquinic acid increased in the composition, the inhibitory effect of the composition on mouse renal cancer cell lines RuCa first increased and then decreased, and the composition in the ratio of 100:0.01 to 100:1 was the best.

4.4.2 Inhibition Rate and Dose-Effect Curve of Each Experimental Group on Mouse Renal Cancer Cell Lines RuCa The inhibition rate of each experimental group on mouse renal cancer cell lines RuCa are shown in Table 2 and FIG. 2.

TABLE 2

The inhibition rate of each experimental
group on mouse renal cancer cell lines RuCa

| Groups | OD value (average) | Inhibition rate (%) |
|---|---|---|
| Chlorogenic acid | 1.248 | 38.45% |
| Coumaroylquinic acid | 1.909 | 5.85% |
| Composition of chlorogenic acid and coumaroylquinic acid (100:0.01) | 0.855 | 57.85% |
| Composition of chlorogenic acid and coumaroylquinic acid (100:0.1) | 0.690 | 65.95% |
| Composition of chlorogenic acid and coumaroylquinic acid (100:1) | 1.005 | 50.42% |
| Composition of chlorogenic acid and coumaroylquinic acid (100:5) | 1.349 | 33.47% |
| Composition of chlorogenic acid and coumaroylquinic acid (100:10) | 1.458 | 28.08% |
| Negative control group | 2.028 | — |

After mouse renal cancer cell lines RuCa were treated with each experimental group, compared with the negative control group, chlorogenic acid single compound had a certain effect on the cell growth; coumaroylquinic acid almost had no effect on the cell growth; however, the composition of chlorogenic acid and coumaroylquinic acid had significant inhibitory effect on the growth of mouse renal cancer cell lines RuCa. When the ratio of two compounds was in the range of 100:0.01 to 100:10, all the compositions could inhibit the growth of mouse renal cancer cell lines RuCa. As the ratio of coumaroylquinic acid increased in the composition, the inhibitory effect of the composition on mouse renal cancer cell lines RuCa increased at first and then decreased. In the ratio of 100:0.01 to 100:1, two compounds had synergistic effect, and the composition at the ratio of 100:0.1 showed the best effect.

5. Conclusion

Chlorogenic acid single compound had a certain effect on the cell growth; coumaroylquinic acid almost had no effect on the cell growth; however, when the ratio of chlorogenic acid and coumaroylquinic acid was in the range of 100:0.01 to 100:10, the composition of them had significant inhibitory effect on the growth of human renal cancer cell lines A498 and mouse renal cancer cell lines RuCa. As the ratio of coumaroylquinic acid increased in the composition, the inhibitory effect of the composition on human renal cancer cell lines A498 and mouse renal cancer cell lines RuCa increased at first and then decreased. When the ratio of two compounds were in the range of 100:0.01 to 100:1, both of them had synergistic effect, and the composition at the ratio of 100:0.1 showed the best effect.

Experimental Example 2 Experiment on the Treatment of Renal Cell Carcinoma In Vitro by Pharmaceutical Composition and its Single Compound According to the results of Experimental Example 1, the combined effect of chlorogenic acid and coumaroylquinic acid (100:0.1) with first-line treatment drugs for renal cancer was further investigated. The experimental and detection methods were the same as those of Experimental Example 1, only the administration schedule was different. The specific administration schedule and results were as follows:

TABLE 3

The inhibition rate of each experimental group on human renal cancer cell lines A498

| Groups | Administration schedule (Final concentration) | Inhibition rate (%) |
| --- | --- | --- |
| Chlorogenic acid | 15 μg/ml | 15.72% |
|  | 30 μg/ml | 37.18% |
|  | 60 μg/ml | 61.34% |
| Coumaroylquinic acid | 15 μg/ml | 1.92% |
|  | 30 μg/ml | 4.85% |
|  | 60 μg/ml | 7.13% |
| Sorafenib | 0.1 μg/ml | 5.36% |
|  | 0.5 μg/ml | 13.81% |
|  | 1 μg/ml | 29.42% |
| Composition 1 | Chlorogenic acid (30 μg/ml) + coumaroylquinic acid (0.03 μg/ml) + sorafenib (0.03 μg/ml) | 72.51% |
| Composition 2 | Chlorogenic acid (30 μg/ml) + coumaroylquinic acid (0.03 μg/ml) + sorafenib (0.15 μg/ml) | 84.92% |
| Composition 3 | Chlorogenic acid (30 μg/ml) + coumaroylquinic acid (0.03 μg/ml) + sorafenib (0.3 μg/ml) | 86.77% |
| Composition 4 | Chlorogenic acid (30 μg/ml) + coumaroylquinic acid (0.03 μg/ml) | 63.19% |

In order to objectively evaluate the synergistic effect of the combination of the three compounds, according to the standard proposed in the non patent literature Chou T C. Theoretical basis, experimental design, and computerized simulation of synergism and antagonism in drug combination studies. [J]. Pharmacological Reviews, 2006, 58 (3): 621-681, whether specific components had synergistic, additive or antagonistic effects was established, and the synergistic effect index of the pharmaceutical composition (Combination Index, CI) was calculated:

$$A/Ae + B/Be + C/Ce = CI$$

A, B and C denote the doses of three components in the pharmaceutical composition; Ae, Be, and Ce denote the dose of a single component required to achieve the tumor inhibition efficiency of the pharmaceutical composition when using a single compound alone. When the CI value is less than 1, it indicates that the components have synergistic effect. The smaller the CI value is, the stronger the synergistic effect is. When the CI value is equal to or greater than 1, it indicates that the components have equivalent or antagonistic effect.

Specifically, Calcusyn software of Biosoft company was used to calculate the CI value, and the detailed results were as follows:

TABLE 4

Synergy index (CI) of each composition

| | Composition 1 | Composition 2 | Composition 3 | Composition 4 |
| --- | --- | --- | --- | --- |
| CI | 0.369 | 0.230 | 0.212 | 0.484 |

It could be seen from the above Table that chlorogenic acid and coumaroylquinic acid had obvious synergistic effect, and when sorafenib was added to the pharmaceutical composition, the synergistic effect among the three was further enhanced. In addition, we also observed that chlorogenic acid, coumaroylquinic acid and sorafenib had a significant synergistic effect on mouse renal cancer cell lines RuCa. On this basis, we investigated whether chlorogenic acid and coumaroylquinic acid had synergistic effect with sunitinib or pazopanib, and against cell lines A498 and RuCa, chlorogenic acid and coumaroylquinic acid had obvious synergistic effect with sunitinib, but the synergistic effect index with pazopanib was only about 1, which indicated that they were only additive effect. The above results indicated that the combination of chlorogenic acid and coumaroylquinic acid could produce obvious synergistic effect with the first-line treatment drugs of renal cell carcinoma, which has a broad clinical application prospect.

Experimental Example 3 Animal Experiment of the Composition and its Single Compound in the Treatment of Renal Cell Carcinoma 1 Experimental
1.1 Test Drugs
  Test drug 1: Chlorogenic acid
  Test drug 2: Coumaroylquinic acid
  Test drug 3: Composition of chlorogenic acid and coumaroylquinic acid (100:0.01)
  Test drug 4: Composition of chlorogenic acid and coumaroylquinic acid (100:0.1)
  Test drug 5: Composition of chlorogenic acid and coumaroylquinic acid (100:1)
  Test drug 6: Composition of chlorogenic acid and coumaroylquinic acid (100:5)
  Test drug 7: Composition of chlorogenic acid, coumaroylquinic acid, and sorafenib (100:0.1:0.5)
1.2 Test Cell Lines
  Mouse renal cancer cell lines RuCa were established by subcutaneously inoculating in mouse axillary. The number of cells inoculated was $1 \times 10^7$, and after inoculation formed transplanted tumor, the cells were passaged in mice for 3 generations for use.
1.3 Test Animals
  80 BABL/C-nu mice, half male and half female, weighing 18-22 g;
2 Experimental Method
2.1 Route of Administration
  intraperitoneal injection (ip)
2.3 Method of Administration
  The tumor tissue in vigorous growth stage was cut into about 1.5 mm³ and homogenized under aseptic conditions to prepare $1 \times 10^7$/ml cell suspension. 80 mice of the above specifications were inoculated subcutaneously in the right armpit with 0.1 ml cell suspension. On the second day after inoculation, the mice were weighed and randomly divided into 8 groups, with 10 mice in each group, that were test drug 1 group, test drug 2 group, test drug 3 group, test drug 4 group, test drug 5 group, test drug 6 group, test drug 7 group, and negative control group. The test drug group was administrated by intraperitoneal injection (ip), 30 mg/kg/time, once a day, and the administration was successively performed 15 times. The negative group was intraperitoneally injected with the same dose of normal saline, once a day, and the mice were weighed before administration.
2.4 Evaluation of Antitumor Effect
  At the end of administration, the experiment was stopped, and the mice were killed by cervical dislocation and weighed. The tumor was stripped, and the tumor inhibition rate was calculated.

Tumor inhibition rate %=[1−(average tumor weight of drug group/average tumor weight of negative group)]×100%

3 Experimental Results

The inhibitory effect of each experimental group on transplanted tumor RuCa in mice was shown in Table 3 and FIG. 3.

TABLE 5

The inhibitory effect of each experimental group on transplanted tumor RuCa in mice ($\bar{x} \pm SD$, n = 10)

| Groups | Dose (mg · kg$^{-1}$) | Body weight Before administration | Body weight 15 d after administration | Tumor weight (g) | Tumor inhibition rate (%) |
|---|---|---|---|---|---|
| Test drug 1 | 30 | 19.6 ± 0.98 | 27.3 ± 1.19* | 1.8 ± 0.14* | 33.33 |
| Test drug 2 | 30 | 19.4 ± 1.17 | 25.2 ± 1.42 | 2.5 ± 0.19 | 7.41 |
| Test drug 3 | 30 | 18.7 ± 0.64 | 26.9 ± 1.58* | 1.0 ± 0.07* | 62.96 |
| Test drug 4 | 30 | 20.8 ± 1.75 | 26.5 ± 1.26* | 0.9 ± 0.08* | 66.67 |
| Test drug 5 | 30 | 21.2 ± 1.08 | 28.5 ± 1.73* | 1.2 ± 0.09* | 55.56 |
| Test drug 6 | 30 | 20.1 ± 1.23 | 27.6 ± 0.97* | 1.9 ± 0.15* | 29.63 |
| Test drug 7 | 30 | 21.6 ± 1.08 | 24.1 ± 1.52* | 0.7 ± 0.21* | 74.07 |
| Negative | N.S | 19.8 ± 1.15 | 24.6 ± 1.47 | 2.7 ± 0.26 | — |

By Oneway ANOVA test, compared with negative group, *P < 0.01.

4 Conclusion

According to the experimental results, compared with the blank control group, chlorogenic acid alone had certain inhibitory effect on mice transplanted tumor RuCa; the antitumor effect of coumaroylquinic acid was not obvious; however, the combination of chlorogenic acid and coumaroylquinic acid had significant inhibitory effect on the growth of transplanted tumor RuCa in mice. When the ratio of chlorogenic acid and coumaroylquinic acid was ranged from 100:0.01 to 100:5, the combination of them had inhibitory effect on the growth of transplanted tumor RuCa in mice. As the proportion of coumaroylquinic acid increased in the composition, the inhibitory effect of the composition on mice transplanted tumor RuCa increased at first and then decreased, and both of compounds showed synergistic effect. Moreover, the composition at the ratio of 100:0.1 showed the best effect. Furthermore, the combination of chlorogenic acid, coumaroylquinic acid, and sorafenib showed the best synergistic effect.

Comparative Example 1 In Vitro Screening of Pharmaceutical Compositions

According to the method of experimental example 1, the present invention investigated other quinic acid derivatives to observe whether there is obvious synergistic effect between quinic acid derivatives and chlorogenic acid on renal cancer cell line RuCa.

The detailed results were as follows:

TABLE 6

The inhibition rate of each experimental group on mouse renal cancer cell lines RuCa

| Groups | Inhibition rate (%) |
|---|---|
| Chlorogenic acid | 37.29% |
| Feruloylquinic acid | 10.42% |
| Cinnamoylquinic acid | 13.94% |
| Composition of chlorogenic acid and feruloylquinic acid (100:0.1) | 38.57% |
| Composition of chlorogenic acid and feruloylquinic acid (100:1) | 39.22% |
| Composition of chlorogenic acid and feruloylquinic acid (100:10) | 33.61% |
| Composition of chlorogenic acid and cinnamoylquinic acid (100:0.1) | 36.27% |
| Composition of chlorogenic acid and cinnamoylquinic acid (100:1) | 37.53% |
| Composition of chlorogenic acid and cinnamoylquinic acid (100:10) | 39.14% |
| Negative control group | — |

The results showed that the combination of chlorogenic acid and feruloylquinic acid or cinnamoylquinic acid had no obvious synergistic effect in inhibiting the proliferation of renal cancer cell lines, which indicated that the synergistic effect of chlorogenic acid and coumaroylquinic acid had strong specificity.

The invention claimed is:

1. A pharmaceutical composition, comprising chlorogenic acid, coumaroylquinic acid, and a targeted drug, wherein the targeted drug is selected from sorafenib, sunitinib, and pazopanib.

2. The pharmaceutical composition according to claim 1, wherein a mass ratio of chlorogenic acid to coumaroylquinic acid is 100:0.01-10.

3. The pharmaceutical composition according to claim 2, wherein the mass ratio of chlorogenic acid to coumaroylquinic acid is 100:0.01-1.

4. The pharmaceutical composition according to claim 1, wherein a mass ratio of chlorogenic acid, coumaroylquinic acid and targeted drug is 100:0.01-1:0.1-1.

5. A pharmaceutical preparation, comprising the pharmaceutical composition according to claim 1 as an active ingredient, and one or more pharmaceutically acceptable excipients.

6. The pharmaceutical preparation according to claim 5, is an oral preparation or an injection preparation.

7. The pharmaceutical preparation according to claim 5, wherein the one or more excipients are selected from one or more of starch, β-cyclodextrin, dextrin, carbomer, microcrystalline cellulose, hydroxypropylmethyl cellulose, low-substituted hydroxypropyl cellulose, sodium carboxymethyl cellulose, polyethylene glycol (PEG), sodium carboxymethyl cellulose, methyl cellulose, ethyl cellulose, mannitol, sodium lauryl sulfate, croscarmellose sodium, lactose, glucose, vitamins, glutathione, folic acid, polyvinylpyrrolidone (PVP), cross-linked polyvinylpyrrolidone, magnesium stearate, talc, colloidal silicon dioxide, aspartame, orange flavor, sodium bisulfite, sodium bicarbonate, sodium carbonate, and enteric coating powder.

8. A method for treatment of kidney cancer, comprising administering the pharmaceutical composition according to claim 1 to a subject in need thereof.

* * * * *